United States Patent [19]

Grutzner et al.

[11] Patent Number: 4,900,421

[45] Date of Patent: Feb. 13, 1990

[54] VORTEX STABILIZED ELECTROPHORETIC SEPARATION APPARATUS

[75] Inventors: John B. Grutzner; Perry J. Pellechia, both of W. Lafayette, Ind.

[73] Assignee: Purdue Research Foundation, West Lafayette, Ind.

[21] Appl. No.: 239,938

[22] Filed: Sep. 2, 1988

[51] Int. Cl.$^4$ ............................................. G01N 27/26
[52] U.S. Cl. ............................... 204/299 R; 204/180.1
[58] Field of Search ............... 204/299 R, 301, 183.2, 204/180.1, 302, 186; 210/222, 748

[56] References Cited

U.S. PATENT DOCUMENTS

| | | |
|---|---|---|
| 4,588,492 | 5/1986 | Bier . |
| 4,642,169 | 2/1987 | Yoshisato et al. .......... 204/299 R X |
| 4,683,042 | 7/1987 | Scott ................................. 204/180.1 |
| 4,790,942 | 12/1988 | Shmidt ....................... 210/321.87 X |

OTHER PUBLICATIONS

W. Y. Tam, John A. Vastano, Harry L. Swinney, and W. Horsthemke, "Regular and Chaotic Chemical Spatiotemporal Patterns", *The American Physical Society* vol. 61, No. 19, 7 Nov. 1988 (p. 2163).

Cornelius F. Ivory, William A. Gobie, James B. Beckwith, Robert Hergenrother, Michael Malec, "Electromagnetic Stabilization of Weakly COnducting Fluids", *Science*, vol. 238, p. 58.

Stellan Hjerten, "Free Zone Electrophoresis", *Chromatog. Rev.*, 9 (1967) 122-219.

Patrick Mattock, Gordon F. Aitchison, Alan R. Thomson, "Velocity Gradient Stabilised, Continuous, Free Flow Electrophoresis. A Review.", *Separation and Purificaton Methods*, 9(1), 1-68 (1980).

John B. Grutzner, Edward A. Patrick, Perry J. Pellechia, and Marisol Vera, "The Continuously Rotated Cellular Reactor", *Journal of the American Chemical Society*, 1988, vol. 110, No. 3, p. 726.

*Primary Examiner*—John F. Niebling
*Assistant Examiner*—John S. Starsiak, Jr.
*Attorney, Agent, or Firm*—Barnes & Thornburg

[57] ABSTRACT

An apparatus for the performance of efficient, large scale separations, particularly electrophoresis and isoelectric focusing, in free solution is described. Inner and outer cylinders define an annular separation chamber for solutions stabilized against convective flow by Taylor vortices generated during rotation of inner cylinder above threshold frequencies. Separation substrates in solution migrate independently in a potential field established between axially distal anodic and cathodic regions of the annular chamber. Axially defined portions of fluid in the chamber identified to contain concentrations of selected substrates are readily separated from other portions of fluid in the chamber.

21 Claims, 2 Drawing Sheets

VORTEX STABILIZED ELECTROPHORETIC SEPARATION APPARATUS

The research leading to the development of this invention was supported in part by a Small Research Grant No. 1 R03 RR03628-O1A1 from the Department of Health and Human Services, Division of Research Resources.

BACKGROUND OF THE INVENTION

This invention relates to electrophoretic separations of chemical species in free solution. More particularly, this invention is directed to an electrophoretic apparatus wherein a liquid support medium in a separation chamber is stabilized against thermal/density gradient induced convective flow by a Taylor vortex regime.

Electrophoretic techniques, such as electrophoresis and isoelectric focusing, have been widely used in modern biotechnology. They are recognized by skilled practitioners as powerful techniques for separation and analysis of proteins and nucleotides, particularly, but also other charged chemical species. The principle of electrophoretic separation is that molecules of different charge and/or size acquire different velocity with respect to a support medium in the presence of an electrical field. A mixture, of various charged molecules will, under the influence of an electrical field, gradually be separated into zones of concentrations of molecules possessing identical migration velocities. In the isoelectric focusing mode, the support medium is prepared to have a pH gradient across the electrical field. The charge on amphoteric molecules in the carrier medium varies with their position in the pH gradient. The molecules move toward the anode or cathode (depending on their charge) until they reach a pH zone within the support medium pH gradient where their net charge is zero—their isoelectric point. Thus molecules having like isoelectric points are focused, i.e. concentrated into the pH regions corresponding to their respective isoelectric points.

One of the principal problems experienced by early users of electrophoretic separation techniques is that associated with convective disturbances in the electrophoretic support medium. The passage of electric current through the electrophoretic medium results in Joule heating of the medium. This heat is dissipated only through the boundaries of the electrophoresis chamber, and a natural consequence is the evolution of temperature, potential and concentration gradients within the medium. Because the density of the medium is a function of temperature, potential and concentration, gradients are established, leading to convective flows. These flows readily disrupt the separation process by mixing of otherwise discrete zones in the medium.

One of the most commonly used techniques to suppress convective mixing in electrophoretic media is the use of so-called anti-convective stabilizers such as coherent or granular gels. The former are most commonly polyacrylamide or agarose and the latter is usually Sephadex. Gels have been used in the preparative applications of each of the three common electrophoretic modes, isoelectric focusing, isotachophoresis, and zone electrophoresis. There are, however, several fundamental problems associated with gel stabilized electrophoretic methods, especially in larger scale preparative applications. The manipulation and preparation of the gel based supports is time consuming and tedious. There is often a problem with adherence of the sample components to the gel which not only results in a decreased recovery but can also cause electroosmosis which has deleterious effects on resolution. In addition, the matrix must be removed from the recovered sample, and cannot generally be reused. Thus, while gel based stabilization methods are adequate for most research laboratory requirements, the upper limit of sample size is wholly inadequate for large scale separations. For that reason and because use of gels introduce complicating factors such as adsorption of analyte to the stabilizer, molecular sieving effects, or tortuosity of migration paths, there has been a significant effort in the art directed toward development of methods and equipment for electrophoretic separations in free solution.

One of the earliest methods to stabilize liquid media against convection was through use of vertical density gradients. A review of the literature will show that practitioners have also attempted to make use of temperature gradients, complicated flow methods, and hydrodynamic pumping. One of the most effective methods, in terms of sample capacity, for large scale electrophoretic methods including electrophoresis and isoelectric focusing, utilizes membranes to define subcompartments in an electrolyzer. The membranes prevent bulk flow between adjacent compartments while allowing free migration of separation substrates. Most recently, Bier and co-workers have combined compartmentalized columns and slow cylinder rotation in a device which has been commercialized as the "Rotofor".

The use of rotation of an electrophoretic separation chamber to stabilize a liquid support medium was used early by Hjerten who carried out zone electrophoresis and isoelectric focusing in a horizontal cylinder having an internal diameter of 3 mm, which is rotated (40 rpm) about the electrophoretic axis. The rotation acts to re-suspend zones of separation substrate which would otherwise sediment due to their higher density. The technique is micro-preparative at best. If the diameter of the cylinder is less than 0.8 mm, no rotation is necessary. The fluid in such a small cylinder is stabilized by its own viscosity and capillary action. Electrophoresis techniques utilizing such small diameter cylinders is referred to in the literature as capillary zone electrophoresis.

Another approach to electrophoretic separations utilizing rotational stabilization of a liquid carrier medium is the "Biostream" separator developed at the Harwell Atomic Energy Institute utilizing a concept originated by Philpot and developed by Thompson. Separation takes place in an annulus between two vertically oriented concentric cylinders. The carrier/support buffer is pumped into the chamber from the bottom. At the top is a stack of "maze plates" that divide the fluid into multiple fractions which in cross-section are concentric rings. Fluid stabilization is achieved by rotation of the outer cylinder at 150 rpm, creating a velocity gradient radially across the annulus, which maintains a laminar flow profile. The walls of the rotor and stator which define the annular space are semipermeable and isolate electrode chambers from the separation chamber.

Because electrophoretic methods conducted in free solution offers significant functional and practical advantages over systems utilizing anti-convective stabilizers, especially in the area of preparative/industrial scale operation, there is a continuing need to develop alternative methodologies for anti-convective stabilization of liquid media under electrophoretic conditions.

Accordingly, it is an object of this invention to provide an apparatus for conducting electrophoretic separations in free fluids utilizing the phenomena of Taylor vortex flow for fluid stabilization against convective mixing.

It is a further object of this invention to provide a method for utilizing the convective circulation of the Taylor vortex to stabilize free liquid electrophoresis media against thermal, concentration and potential transients.

It is still another object of this invention to provide a construction for an apparatus for the performance of electrophoretic separations which can be scaled up directly from analytical (microliter) to industrial (multiliter) scale.

A separation apparatus usable for electrophoretic separations, including particularly zone electrophoresis and isoelectric focusing, in free liquids is provided. The apparatus is constructed to have a substantially uninterrupted annular chamber adapted to contain a support fluid and separation substrates capable of migrating relative to said fluid under the influence of an electrical field. The annular chamber is defined by walls of an outer cylinder and a substantially coaxial, rotatably mounted inner cylinder. Preferably at least one of the cylinders is a right circular cylinder. The inner cylinder can be in the form of a solid cylinder or a tube having an outer diameter less than the inner diameter of the outer cylinder at respective axially aligned locii.

The annular chamber is provided with means for applying an electrical field between axially remote anodic and cathodic regions of the chamber. The electric field is preferably applied through electrodes in current conducting communication with the respective anodic and cathodic regions of the annular chamber. The electrodes can be in direct contact with a support fluid in the chamber or, preferably, each electrode is positioned in an electrolyte, itself in current conducting communication with the support fluid. The electrolyte in contact with each electrode can be separated from the support fluid by an electrical current transmitting membrane structure, such as a porous glass membrane or a semipermeable membrane.

The separation apparatus also includes a means for rotating the inner cylinder relative to the outer cylinder at a rotational frequency (F) where F is at least as high as the critical frequency ($F_c$) for the onset of Taylor vortex flow in the annular chamber. The critical frequency for any given apparatus can be calculated from the formula provided hereinbelow. The critical Taylor vortex frequency is unique to each separation apparatus dependent on specific physical parameters unique to that apparatus and the viscosity of the support fluid in the annular chamber. The inner cylinder is preferably rotated utilizing a variable speed stepping motor. The preferred rotational frequency of the inner cylinder during use of the separation apparatus is $F_c \leq F < 10 F_c$. Higher rotational frequencies can be utilized, but without known advantage.

The present separation apparatus is also equipped with means for separating fluid in axially discrete portions of the annular chamber from fluid in other axially discrete portions of the annular chamber. In a preferred embodiment the fluid separation means includes a valved elution port communicating with the separation chamber and positioned so that at least a portion of the fluid can be eluted from the annular chamber through the port by gravity flow when the chamber is in a vertical orientation. Preferably the valved outlet is located at or near an axial end of the annular chamber and thus proximal to the lowest point of the annular chamber when situated in a vertical orientation.

Alternatively, the means for separating axially discrete portions of fluid in the chamber includes a port located proximal to an axial end of the annular chamber which is the uppermost end of the chamber in vertical orientation. Axially defined portions of the fluid in the annular chamber can be removed, for example by a syringe inserted through said port and used to withdraw axially discrete portion of the fluid in the chamber. The upper port can optionally serve also as a vent for gases formed at the electrodes during apparatus operation when the electrodes are positioned in the chamber.

In a preferred embodiment the anodic region and cathodic region of the annular chamber are each located proximal to a respective opposite axial ends of the annular chamber so that the electric field spans substantially the entire axial length of the chamber.

Optionally the separation apparatus of this invention can include means for controlling temperature of the fluid contained in the annular chamber. Thus in a simple embodiment the temperature control means can include a coolant jacket in thermal communication with a wall of the chamber. Liquid of predetermined temperature can be circulated through the coolant jacket, for example, to minimize temperature increase of the support fluid during performance of electrophoretic separation in the apparatus. Temperature control can be especially important when the separation substrates are known to be thermally labile.

The separation apparatus can also be equipped with a means for detecting the axial locii of discrete concentrations of separation substrates in the support fluid. Thus, for example, the apparatus can be designed to accommodate a traveling light source and detector which can be moved axially along the length of the annular chamber to detect axially defined portions of support fluid which contain concentrations of separation substrates. Where such a detection system is used, it is preferred that the outer cylinder be formed at least partially from an optically transparent material, preferably quartz glass, to allow transmission of a broad range of UV and visible radiation.

Alternatively, a detection means for substrate concentrations can be utilized to analyze the support fluid as it is eluted from the separation chamber through the valved elution port. Thus the valved port can be equipped with a flow cell which includes a sensor capable of measuring, for example, pH, conductivity, or optical properties of fluid flowing from the separation chamber and through said flow cell. The signal from the sensor in said flow cell can be displayed graphically or utilized to trigger a fraction collector pre-programed to collect effluent volumes exhibiting sensed substrate concentrations above predetermined threshold values. The apparatus can be utilized in an isoelectric focusing mode wherein pH gradient-generating ampholytes are combined with the support fluid to establish a predetermined pH gradient between the anodic and cathodic regions of the annular chamber. In that mode of operation a compound of known isoelectric point can be isolated from support fluid fractions by collecting those fluid volumes having a pH corresponding to the compound's isoelectric point. Such volumes can be detected utilizing a pH sensing flow cell mounted on the elution port.

The Taylor vortex flow stabilized separation apparatus in accordance with this invention, is operated utilizing general operating procedures and techniques which have been utilized for electrophoretic separations in free fluid electrophoretic separation devices in the prior art. Thus positioning of electrodes, loading of samples, selection of support fluid composition (for example, buffer strength, buffer components, pH), selection of support fluid additives (for example, ampholytes, surfactants/surfactant micelles, urea, non-ionic densiometric agents, and the like) can be selected and utilized based on the same criteria for their selection and use in art-recognized separation equipment for electrophoretic separations in free fluid.

The present separation apparatus can be utilized to effect electrophoretic separation of a wide variety of chemical species ranging from metal ion species to amino acids, proteins, nucleotides and polynucleotides, viruses, bacteria and other whole cells. The significance of such broad application of the performance of electrophoretic methods utilizing the present apparatus is further highlighted by the fact that the Taylor vortex stabilization phenomena is such that the apparatus can be readily constructed to commercial scale specifications without loss of function or efficiency of operation.

DETAILED DESCRIPTION OF THE INVENTION

Figure 1:
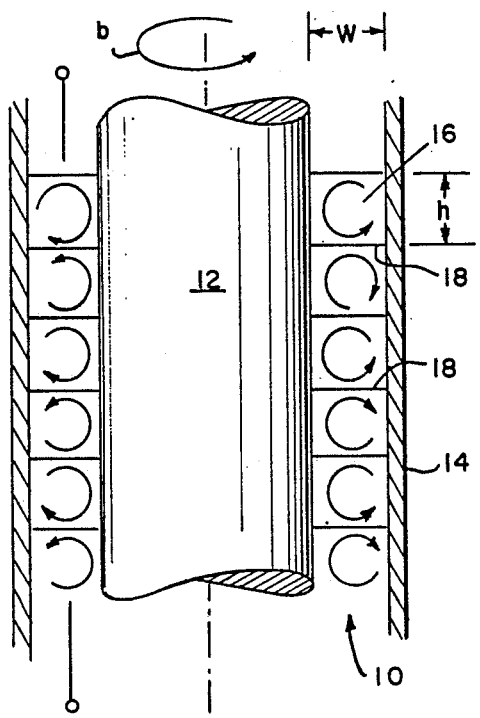
FIG. 1 is a diagrammatic view of an annular chamber illustrating formation of Taylor vortex cells.

With reference to FIG. 1, Taylor vortex flow is generated in a liquid contained in an annular gap 10 between an inner cylinder 12 and a concentric outer cylinder 14 when the inner cylinder 12 is rotated relative to the outer cylinder 14 above a critical frequency. The phenomena is one of the paradigms of fluid dynamics and has been widely investigated and reported in the art. The vortex consists of liquid cells 16 whose height h is approximately equal to the width w of the annular gap 10. The major flow of the liquid in annular gap 10 is azimuthal flow of the liquid in the same sense as the rotation of inner cylinder 10 (as shown by arrow b). Nuclear magnetic resonance studies have shown that the vortex radius is approximately half the cell height and the vortex axial angular velocity is approximately equal to $F_c$ when F is twice $F_c$. Within each cell 16, a rotating vortex core of liquid is established, and adjacent cells are counter-rotating. This creates sharp stable boundaries 18 which alternatively flow inward (slow) and outward (fast). The number of cells in a column is equal to the column length divided by the cell height with roundoff occurring in the end cells. Most of the studies performed to date on prototypes of the present apparatus have been carried out with a gap ratio (inner/outer cylinder radii) of about 0.5. It has been found that the rotation rate may be varied over an order of magnitude before the onset of more complex motions in the fluid. Vortex stabilized columns have been generated and maintained in devices ranging from a 50 microliter syringe with a central melting point capillary serving as the inner cylinder up to an 8 liter cylinder.

The practical size range of the inner and outer cylinders (and thus the volume of the annular gap) is linked to the critical frequency for the onset of Taylor vortex flow. The critical Taylor frequency is defined as $$T_C = [4q/(1+q)][(2\pi F_C a d/\nu)^2(d/a)] = 6199.1.$$

for q=0.5 where q is the gap ratio, d is the gap width, a the inner cylinder radius, F the rotor frequency and $\nu$ is the kinematic viscosity. For water $\nu=1$ cS, and this gives the critical frequency $F_c$ as $$F_c = 68.16\nu/2\pi a^2 \simeq 0.1085/a^2$$

For lab operations, F is normally limited to 0.01 to 100 Hz so "a" is in the range of 3 cm to 0.3 mm. The corresponding annular volumes are N×283 ml to N×0.283 microliters where N is the number of cells in the annular chamber. Taylor vortex flow is maintained over the frequency range from $F_c$ to at least 10 times $F_c$ in separation devices constructed in accordance with this invention over a wide range of annular volumes. It has been reported in the literature that some Taylor vortex structure is maintained at rotational frequencies approaching 10,000 times the critical frequency. With gap ratios approaching unity, and large diameter cylinders, it is possible to reduce the critical frequency. For example, to create 1 mm cells, one can choose a gap ratio of 0.5 and 2 mm internal diameter tubing which has a critical frequency close to 100 Hz. The critical frequency can be reduced to 2 Hz with a gap ratio of 0.8 inside 1 cm internal diameter tubing. Industrial scale operation could be achieved by using large diameter cylinders with q near 1, i.e., a small gap. This would give a practical $F_c$ value for large volumes.

Figure 2:
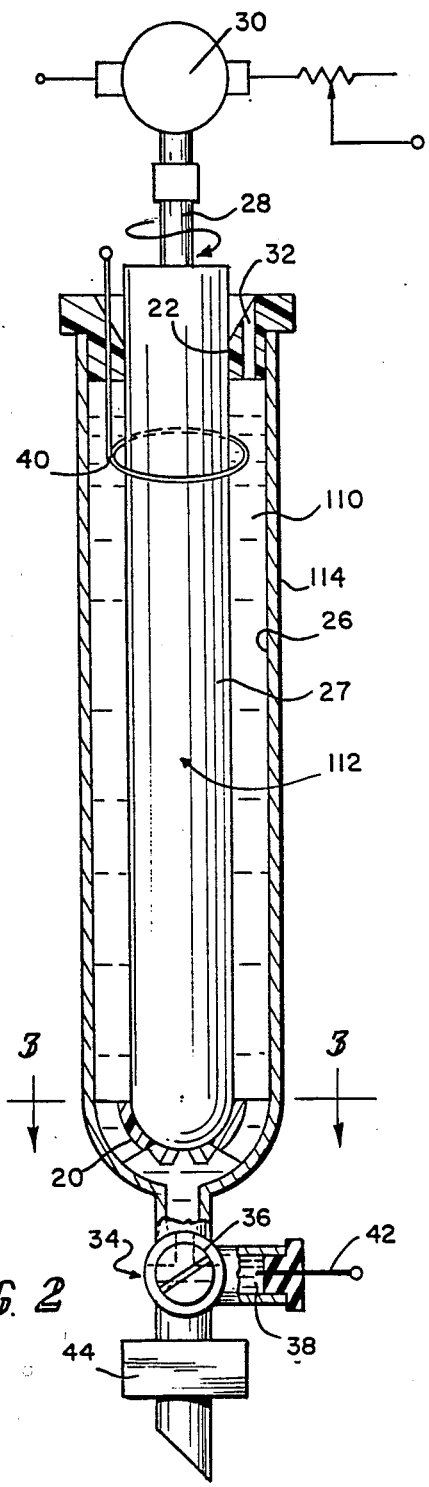
FIG. 2 is a sectional view of a vortex stabilized separation apparatus of this invention.

FIG. 2 illustrates a simple operational embodiment of the present invention. Inner cylinder 112 is rotatably supported in outer cylinder 114 by lower inner cylinder support 20 and upper cylinder guide 22 which also serves as a closure for the annular separation chamber 110 defined by the walls 27 and 26 of the inner cylinder 112 and outer cylinder 114, respectively. Inner cylinder 112 is connected through drive shaft 28 to a variable speed motor 30 positioned to rotate inner cylinder 112 relative to outer cylinder 114. Upper cylinder guide 22 includes a vent 32 which also serves as a means for accessing annular chamber 110 for the purpose of sample input and withdrawal by use of, for example, a syringe (not shown). Separation chamber 110 is provided with an elution port 34 with "T" valve 36 which can be positioned to allow elution of fluid in the annular chamber by gravity flow out elution port 34 or to allow liquid communication between separation chamber 110 and electrode compartment 38 (the position shown).

The lower inner cylinder support 20 is designed to allow fluid in separation chamber 110 to pass through elution port 34 when valve 36 is positioned to allow elution of the fluid from the separation chamber 110 (about ¼ turn counterclockwise from the position shown).

Figure 3:
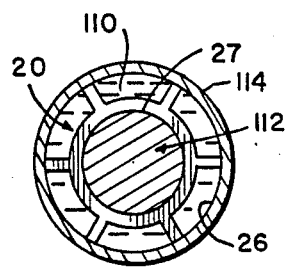
FIG. 3 is a cross-sectional plan view of the apparatus in FIG. 2 at 3—3 showing the flow through design of the lower inner cylinder support.

FIG. 3 is a cross-sectional plan view of the apparatus of FIG. 2 at 3—3. The inner cylinder support 20, located in the lower portion of annular separation chamber 110, has a segmented of spider-type construction to allow fluid in separation chamber 110 to pass into elution port 34 with minimal mixing of fluid in adjacent Taylor vortex cells formed in the separation chamber during rotation of inner cylinder 112 above the critical frequency. The inner cylinder support construction also allows elution of fluid from annular separation chamber 110 during rotation of inner cylinder 112.

An electrical field is applied to fluid in separation chamber 110 by upper electrode 40 and lower electrode 42 positioned in electrode compartment 38, which during operation of the apparatus is in fluid communication with the support fluid in separation chamber 110. Notably, gas bubbles formed at lower electrode 42 during operation of the apparatus shown in FIG. 2 cause but minimal transient perturbation of the Taylor vortex cells as they flow up through the annular separation chamber.

The elution port 34 is be fitted with a flow cell 44 having a sensor capable of detecting and signalling concentrations of separation substrates in the support fluid as it passes through elution port 34.

Control of temperature in the separation chamber can be facilitated, for example, by constructing the apparatus to have a coolant jacket in thermal contact with a cylinder wall.

Figure 4:
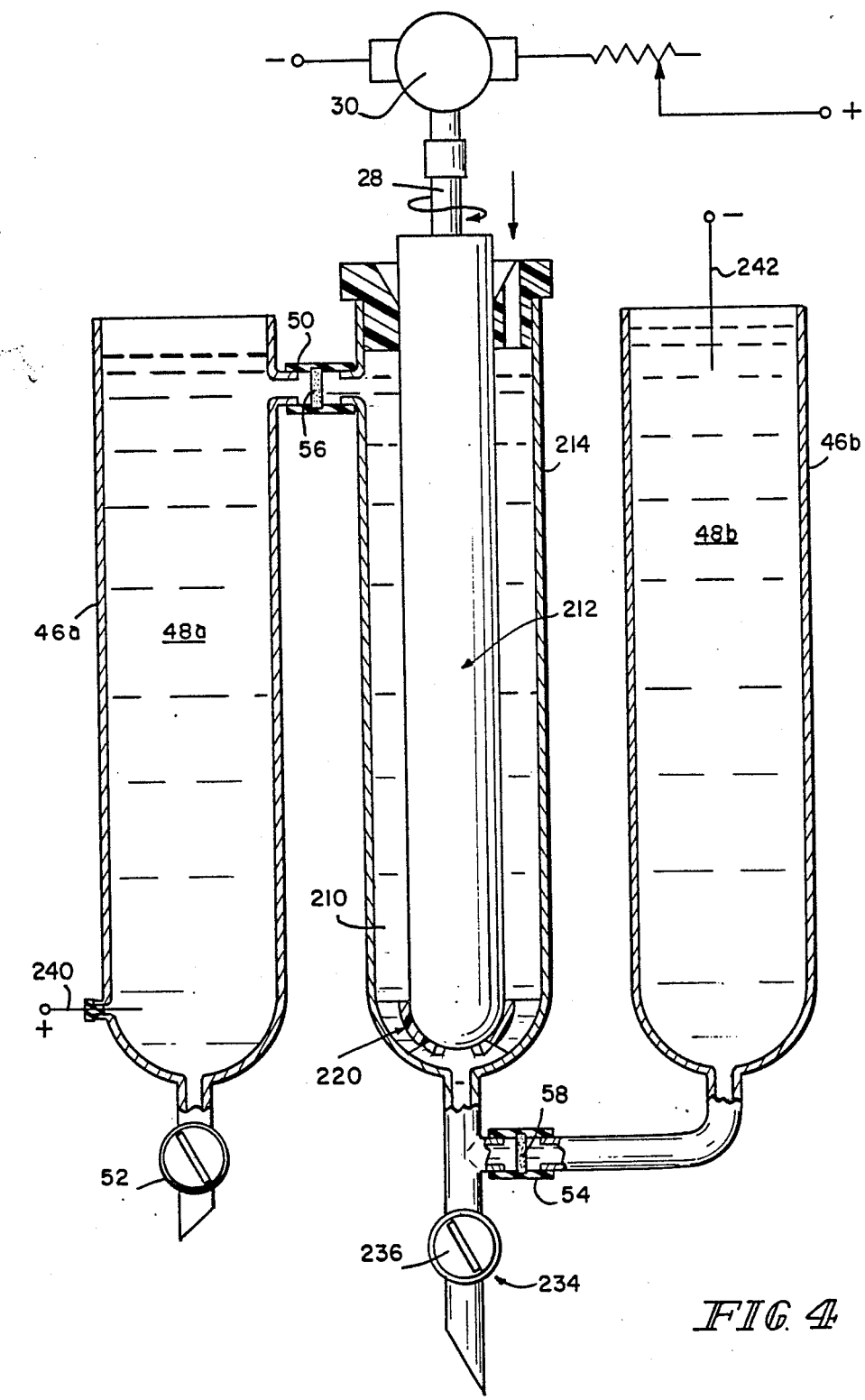
FIG. 4 is a sectional view of another apparatus embodiment of this invention.

FIG. 4 depicts another embodiment of the present invention. The apparatus is identical to that illustrated in FIG. 2 except that electrodes 240 and 242, used to apply an electric field to the annular separation chamber 210 between the rotatably mounted inner cylinder 212 (supported by inner cylinder support 220) and the outer cylinder 214, are each mounted in separate electrode compartments 46a and 46b for containing electrolytes 48a and 48b, respectively. Each electrolyte has a composition dependent on the nature of the electrode (anode vs cathode) the pH or pH range of the support fluid and the nature of the electrophoretic method being performed. This construction (with separate electrode compartments) allows electrodes 240 and 242 to be removed from direct contact with the support fluid, the separation substrate, and any support fluid additives and offers the advantage of minimizing both oxidation/reduction of support fluid components (the pH of the conducting solution can be selected to repel ampholytes) and physical disturbance of the support fluid by gas bubbles produced at the electrodes during operation of the apparatus.

Electrode compartments 46a, 46b are each constructed so that electrolytes in said compartments are in current conducting communication with support fluid in annular chamber 210. Electrode compartment 46a is constructed to contain electrolyte 48a which is in contact with electrode 240 and in current conducting communication with the fluid in separation chamber 210 through upper electrode tube 50. Valve 52 on electrode chamber 46a can be opened to drain electrolyte 48a from the chamber. An electrolyte 48b in electrode compartment 46b is in contact with electrode 242 and in current conducting communication with fluid in annular separation chamber 210 through lower electrode tube 54. Valve 236 can be rotated manually to allow elution of fluid in separation chamber 210 through elution port 234.

Electrode tubes 50 and 54 are each fitted with a current conducting membrane structure 56, 58, respectively, for example, a porous glass plug or a semi-permeable membrane, to prevent hydrodynamic mixing of electrolytes 48a and 48b with support fluid in annular separation chamber 210.

The nature of the electrolytes in each of the respective electrode compartments 46a, 46b will depend on which compartment is selected as the anode compartment and which is selected as the cathode compartment. The electrolytes utilized in the electrode compartment designated for the anode is acidic, typically a dilute acid or a buffered acidic solution, The electrolyte utilized in the electrode component selected for the cathode is typically basic and commonly buffered.

The operation of the present electrophoretic separation apparatus parallels the operation of art-recognized electrophoretic separation equipment known in the art, particularly those devices utilizing a free fluid support medium stabilized by means other than the Taylor vortex flow utilized in the present apparatus. Thus the same operational considerations apply as those for the performance of electrophoretic separations in, for example, a sucrose density gradient stabilized electrophoretic separation apparatus, such as the well-known Ampholine electrofocusing column, the Disco Model 210 density gradient electrophoresis column, or the Poly-Prep 200. Operation of the apparatus of the present invention differs only in the requirement that the inner cylinder be rotated at or above the critical frequency during the electrophoretic separation. During isolation of portions of the support fluid bearing concentrations of selected separation substrates rotation should be reduced below $F_c$ (80–95% $F_c$). This reduces the rate of dispersion, i.e., diffusion of the analytes present, thus preserving the separation.

When the electrophoretic separation apparatus of this invention is to be operated in a zone electrophoresis mode, a sample containing multiple separation substrates is transferred to the separation chamber, already containing support fluid, for example, a buffer of predetermined pH and ionic strength, with the inner cylinder being rotated at a frequency above the critical frequency, and with care to apply the sample as a narrow band occupying a minimum number of vortex cells. The sample can be applied to the stabilized support fluid in the separation chamber using, for example, a syringe inserted into the chamber, at any locus along the chamber axis. An electric field is applied to the separation chamber for a period of time sufficient to allow differential migration of the separation substrates in the sample. The electrodes (40, 42 of FIG. 2; 240, 242 of FIG. 4) are connected to a power supply, commonly a constant voltage power supply. Axially discrete defined portions of support fluid bearing elevated concentrations of migrated separation substrates can be detected in the annular chamber by, for example, an axially moveable optical sensor designed to measure optical properties of fluid in the respective vortex cells along the axial length of the annular chamber. The inner cylinder is rotated continuously throughout the electrophoretic separation procedure. During elution of separation substrate bearing fractions from the separation chamber, reduction of rotational frequency, as described above, is preferred.

In the isoelectric focusing mode the separation apparatus of this invention is operated in much the same manner as that described above for zone electrophoresis. However, because isoelectric focusing is an equilibrium method, the way the sample is applied is not as critical as in zone electrophoresis where a thin starting zone is necessary. Thus, the separation sample may be incorporated (mixed) into the support fluid before or after it is filled into the separation chamber. Also, because isoelectric focusing depends on the formation and maintenance of a pH gradient in the electric field, pH gradient producing additives, for example, art-recognized ampholytes, are added to the support fluid at pH gradient producing concentrations, typically about 1%. The progress of focusing can be observed by decrease of current at a constant voltage. The preferred mode of operation of the focusing apparatus is at constant power. During a separation run the electric field may initially start at about 5 to 10 volts per centimeter and gradually increase up to as much as 100 volts per centimeter as the conductivity of the focused medium decreases. The focused concentrations of separation substrates can be detected and isolated by elution of the fluid portions containing such concentrations from the separation chamber.

Taylor vortex flow stabilization of the support fluid in a electrophoretic device offers multiple inherent advantages. Significantly, the vortex flow enhances dissipation of thermal energy from the support fluid to the chamber walls. Not only does this minimize the possibility of having localized zones of support fluid at substrate denaturing temperatures, but it also allows for generally more efficient cooling which may allow steeper voltage gradients and increased resolution power. Further, the vortex flow tends to minimize the potential for formation of undesirable neutral zones that are known to occur in gel stabilized isoelectric focusing media.

The present apparatus may allow for the preparative/commercial scale electrophoretic separation of a wide variety of substrates with the high separation efficiencies recently heralded by skilled practitioners for capillary zone electrophoresis. Further, the use of Taylor vortex stabilization can allow the establishment and maintenance of pH gradients without use of art-recognized ampholytes. It is possible that isoelectric focusing can be achieved in the present apparatus using support fluids free of polymeric ampholytes, thus eliminating the need to separate focused substrates from their equi-isoelectric ampholytes. Probably one of the earliest commercial applications of the present apparatus will be its use for the isolation, purification and standardization of ampholytes for use in other electrophoretic applications. Thus, a solution of a crude ampholyte preparation can be introduced into the annular chamber of the present invention, focused in the electrical field and then separated according to pre-determined pH values. Since purification of ampholyte preparations constitute a significant portion of the expense of their production, it is expected that use of the present separation apparatus can provide a significant reduction in the cost of manufacture of those compositions.

The separation apparatus of this invention has been described particularly for electrophoretic separation. It will be appreciated, however, by those skilled in the art that potential fields other than an electrical field can be utilized to effect selective differential migration of separation substrate species in a support fluid stabilized by Taylor Vortex flow. Thus, means for applying for example, a magnetic potential, a centrifugal potential, or a chemical potential along the length of the separation chamber can be substituted for the electrical potential field herein detailed for the separation of substrates which migrate differentially with respect to the support fluid in response to such potential field.

While each of the illustrations herein depict the present apparatus in a vertical operational orientation, it is noted that the apparatus can be designed to be operated in a horizontal orientation. Such a design requires use of fluid retaining axial seals where the rotatably mounted inner cylinder contacts the cylinder guide at the end of the separation chamber. As presently contemplated, however, a vertical operational orientation is preferred for the reason that such axial seals are not required, and the vertical orientation allows the separation of fluid fractions containing migrated separation substrates by gravity flow.

EXAMPLES

EXAMPLE 1

Taylor Vortex Study-Maintenance of pH Gradient

An apparatus was constructed substantially as shown in FIG. 2 having an inner cylinder (outer diameter 1.8 cm) rotatably mounted inside an outer cylinder having an internal diameter of 2.5 cm. The critical frequency for water in this system is 22.1 rpm. The annular separation chamber was filled (60 ml) with a 1% solution of Fisher Universal Indicator. The inner cylinder is rotated at 60 rpm utilizing a variable speed stepping motor. The column length is 25 cm. The apparatus is enclosed in a plexiglass box fitted with a cooling fan. Electrolysis is performed at constant voltage of 2 KV utilizing an upper platinum loop anode and a lower platinum wire cathode mounted in the column terminator. Immediately after initiating current flow the indicator evidenced formation of acidic (red) and basic (blue-purple) regions at the anode and cathode respectively. The regions are characterized by sharp boundaries orthogonal to the axis of the annular chamber. The length of the respective acidic and basic regions were such that the acid region was approximately twice the length of the basic region, said lengths being directly proportional to the electrophoretic mobilities of the hydronium ($h_3O^+$) and hydroxyl ($-OH$) ions respectively. After about 15 minutes of applied potential, the system reached an equilibrium point. The individual vortex cells in the region close to the neutralization level are clearly discernible. The pH=7 neutral region occupies about five vortex cells. Minor variation from the horizontal cell boundaries are observed from time to time when, for example, bubbles rise through the layers. When the potential is removed, the neutralization boundary shifts to the midpoint of the column as expected for equimolar electrolytic generation of $H_3O^+$ and $-OH$.

Molecular transport takes place in the time sequence- fast azimuthal equilibrium corresponding to cylinder rotation frequencies; moderate axial transport with transfer preferentially at the cell boundary; and slow radial equilibrium which is facilitated by azimuthal/axial transport under electrolytic conditions. It appears that transport is more effective across the slower moving inward flowing boundary than it is across the fast outward boundary. The acid and base bands advancing into the neutral solution are alternatively wide (slow) and narrow (fast).

Transport in the column is controlled by electromobility. The time for column development can be decreased by a factor of 5 by the addition of KCl. This also narrows the neutral region of the column to a single vortex cell. Equilibrium current is independent of rotor frequency over an order of magnitude (30–300 rpm).

Again, the location of the neutral cell in the column is biased to the basic end of the column and reflects the higher mobility of the proton (hydronium ion) relative to the hydroxide ion. In one mM KCl solution the neutral cell is located at 0.65±0.06 of the inter electrode distance. The theoretical location of the neutral cell is 0.61 based on the mobilities of H, $^+Cl^-$, $K^+$ and $^-OH$.

EXAMPLE 2

Electrophoresis

In the same apparatus utilized in Example 1, electrophoresis of 0.01M Tris/0.003M HCl solution was conducted. The solution contains 1% Fisher Universal Indicator for visualization. The electrodes are reversed from the positions utilized in Example 1 so that the cathode is at the top of the column and the anode is located at the bottom of the column. Electrolysis was performed at 10 watts constant power (1550 V, 6.9 mA). The solution clears from the cathode toward the anode as electrophoresis of the indicator takes place. The acid boundary location and base boundary location, measured at 2 minute time intervals, were as follows:

| BASE INTERFACE (IN) | ACID INTERFACE (IN) | TIME (MIN) |
| --- | --- | --- |
| 10.8 | 3.3 | 2 |
| 9.8 | 3.6 | 4 |
| 8.7 | 4.1 | 6 |
| 7.9 | 4.6 | 8 |
| 6.2 | 5.0 | 10 |
| 5.6 | 5.0 | Equilibrium |

EXAMPLE 3

Isoelectric Focusing

In an apparatus similar to that shown in FIG. 4, the right hand electrode compartment was fitted with a platinum anode and filled with 0.05M phosphoric acid. The left hand column was fitted with a platinum cathode and filled with 0.05M sodium hydroxide. The cathode compartment was connected to the top of the separation column by 1 cm tubing (with no membrane structure) and the anode compartment is similarly connected at the bottom of the separation column through a "T" valve on the elution port. The inner cylinder OD was 1.8 cm and the outer cylinder ID is 2.5 cm (critical frequency for water-22.1 rpm). The inner cylinder was rotated at 60 rpm. The annular separation chamber (about 25 cm long) was then charged with 60 ml of 1% Biorad ampholyte (range pH 3-10) and 100 mg of hemoglobin, Hb (pI 6.9) and 100 mg cytochrome C (pI 9.6). Isoelectric focusing was conducted at 10 watts for 6 hours (final current 5 mA), to effect a band separation of 8.5 cm and band widths of approximately 4.5 cm. Band focusing was effectively complete after 2 hours as judged by the time dependence of the current flow and the observed band concentration.

EXAMPLE 4

Isoelectric Focusing of IEF Standards

The isoelectric focusing of the 8-component Biorad IEF standard to which a small amount of methyl red was added in a 1% ampholyte solution (Biorad pH 3-10) was carried out under the same conditions as stated in Example 3 above except that the electropolarity and buffer solutions were reversed. After 2 hours, focused bands of methyl red (pI 3.75) and phycocyanin C (blue pI 4.65) are visible. The methyl red and phycocyanin are separated by 2.6 cm with band widths of 6.5 cm and 2.5 cm, respectively. The separation was accomplished in 2 hours at 10 watt constant power (600-1700 V).

The different band widths of the two components reflect the different diffusion constants of those components (methyl red-molecular weight 269; phycocyanin-molecular weight 232,000). The estimated band width ratio 2.6±0.6 is compared with the value of 3.08 predicted from the equations of Svennson assuming Stokes-Einstein diffusion. The bands are stable for hours.

We claim:

1. A separation apparatus comprising
   a substantially uninterrupted annular chamber defined by walls of an outer cylinder and a substantially coaxial rotatably mounted inner cylinder, said annular chamber adapted to contain a support fluid and separation substrates capable of migrating relative to said fluid under the influence of an electrical field,
   means for applying an electrical field to said chamber to generate an anodic region and an axially remote cathodic region in the annular chamber,
   means for rotating the inner cylinder relative to the outer cylinder at a rotational frequency (F) where F is at least as high the critical frequency ($F_c$) for onset of Taylor vortex flow in the annular chamber, and
   means for separating fluid in axially discrete portions of the annular chamber from fluid in other axially discrete portions of the annular chamber.

2. The separation apparatus of claim 1 wherein the anodic region and cathodic region are located proximal to the respective opposite axial ends of the annular chamber.

3. The separation apparatus of claim 1 where $F_c \leq F < 10 F_c$.

4. The separation apparatus of claim 1 further comprising means for controlling temperature of the fluid contained in the annular chamber.

5. The separation apparatus of claim 4 wherein the temperature control means includes a coolant jacket in thermal communication with a wall of the annular chamber.

6. The separation apparatus of claim 1 wherein at least one of the cylinders is a right circular cylinder.

7. The separation apparatus of claim 6 wherein both the inner and outer cylinders are right circular cylinders.

8. The separation apparatus of claim 7 further comprising means for detecting the axial locii of concentrations of separation substrates in the support fluid.

9. The separation apparatus of claim 8 wherein the detecting means includes a sensor capable of measuring PH, conductivity, or optical properties of fluid in axially defined portions of the annular chamber.

10. The separation apparatus of claim 1 further comprising means for identifying axial discrete portions of support fluid which contain concentrations of separation substrates.

11. The separation of claim 1 wherein the electric field is applied through electrodes in current conducting communication with the respective anodic and cathodic regions of the annular chamber.

12. The separation apparatus of claim 11 wherein the electrodes are in contact with the support fluid.

13. The separation apparatus of claim 11 wherein each electrode is positioned in a current conducting fluid, each in current conducting communication with the support fluid.

14. The separation apparatus of claim 13 wherein the current conducting fluid is separated from said support fluid by an electrical current transmitting membrane structure.

15. The separation apparatus of claim 1 wherein the means for separating axially discrete portions of the fluid in the annular chamber includes a valved elution port communicating with said chamber so that at least a portion of the fluid can be eluted from the annular chamber through said port by gravity flow when the annular chamber is in a vertical orientation.

16. The separation apparatus of claim 15 further comprising means for detecting substrate concentrations in fluid passing through the valved outlet.

17. The separation apparatus of claim 16 wherein the detecting means is a flow cell communicating with the valved outlet said flow cell including a sensor capable of measuring pH, conductivity or optical properties of fluid flowing through said flow cell.

18. A separation apparatus comprising
a substantially uninterrupted annular chamber defined by walls of an outer cylinder and a substantially coaxial rotatably mounted inner cylinder, said annular chamber adapted to contain a support fluid and separation substrates capable of migrating relative to said fluid under the influence of a force field, means for applying a force field to said chamber to generate in said chamber a region of first potential and an axially remote region of second potential, means for rotating the inner cylinder relative to the outer cylinder at a rotational frequency (F) where F is at least as high as the critical frequency ($F_c$) for onset of Taylor vortex flow in the annular chamber, and means for separating fluid in axially discrete portions of the annular chamber from fluid in other axially defined portions of the annular chamber.

19. The separation apparatus of claim 18 wherein the force field is an electrical field.

20. A method for separating substrates which migrate with respect to a support fluid under the influence of a potential field said method comprising the steps of
transferring said substrates in a support fluid to an annular chamber defined essentially by walls of an outer cylinder and a substantially coaxial rotatably mounted inner cylinder, rotating the inner cylinder relative to the outer cylinder at a rotational frequency (F) where F is at least as high as the critical frequency ($F_c$) for onset of Taylor vortex flow in the fluid in the annular chamber, and during said rotation applying a potential field axially to said chamber to generate in said chamber a region of first potential and an axially remote region of second potential, said potential field being applied until at least one axially discrete portion of support fluid in the chamber is detected to contain a concentration of a substrate, and separating said axially discrete portion of substrate containing-support fluid in the annular chamber from other portions of fluid on the chamber.

21. The method of claim 20 wherein the potential field is electrical.

* * * * *